United States Patent
Palmer

(10) Patent No.: US 10,206,810 B2
(45) Date of Patent: Feb. 19, 2019

(54) APPARATUS FOR SEXUAL ACTIVITY USAGE

(71) Applicant: Carolyn Palmer, Oshawa (CA)

(72) Inventor: Carolyn Palmer, Oshawa (CA)

( * ) Notice: Subject to any disclaimer, the term of this patent is extended or adjusted under 35 U.S.C. 154(b) by 144 days.

(21) Appl. No.: 15/237,613

(22) Filed: Aug. 15, 2016

(65) Prior Publication Data
US 2017/0042726 A1    Feb. 16, 2017

Related U.S. Application Data

(60) Provisional application No. 62/204,761, filed on Aug. 13, 2015.

(51) Int. Cl.

| | | |
|---|---|---|
| *A61F 6/06* | (2006.01) | |
| *A61F 6/04* | (2006.01) | |
| *A61F 6/02* | (2006.01) | |
| *A61F 7/00* | (2006.01) | |
| *A41B 9/12* | (2006.01) | |

(52) U.S. Cl.
CPC ............... *A61F 6/06* (2013.01); *A61F 6/02* (2013.01); *A61F 6/04* (2013.01); *A61F 7/00* (2013.01); *A41B 9/12* (2013.01); *A61F 2006/041* (2013.01); *A61F 2006/048* (2013.01); *A61F 2007/0048* (2013.01)

(58) Field of Classification Search
CPC ...... A61F 6/02; A61F 6/04; A61F 6/06; A61F 2006/041; A61F 2006/048; A41B 9/12
See application file for complete search history.

(56) References Cited

U.S. PATENT DOCUMENTS

| | | | | |
|---|---|---|---|---|
| 4,981,147 A | * | 1/1991 | Barnett | A61F 6/04 128/830 |
| 5,620,429 A | * | 4/1997 | Al-Saleh | A61F 6/065 600/38 |
| 2007/0186935 A1 | * | 8/2007 | Wang | A61F 6/04 128/844 |
| 2008/0230073 A1 | * | 9/2008 | Nan | A61H 19/50 128/844 |
| 2013/0133665 A1 | * | 5/2013 | Waller | A61F 6/02 128/830 |
| 2014/0039432 A1 | * | 2/2014 | Dunbar | A61F 13/49003 604/360 |
| 2015/0022328 A1 | * | 1/2015 | Choudhury | G06F 3/04847 340/12.5 |

(Continued)

FOREIGN PATENT DOCUMENTS

JP        2007054581 A   *  3/2007

*Primary Examiner* — Kristen Matter

(57) ABSTRACT

A garment assembly useful for sexual intercourse between a first user and a second user when the penetration of a body-extending member into a body orifice is either not possible or unwanted. The garment assembly includes a front and back panel covering and a crotch piece with the appearance of an ordinary garment normally found in a public environment such as one having the appearance of underwear. A fluid-impenetrable receiver attached to the front panel of the garment assembly will operate as a substitute for a body-orifice. The receiver includes an entryway adjoined to an interior cavity sized to accommodate a body-extending member. A preferred interior cavity includes sexually-interactive textured material for engagement with the body-extending member during use.

14 Claims, 12 Drawing Sheets

(56) References Cited

U.S. PATENT DOCUMENTS

2015/0142088 A1* 5/2015 Riva Godoy ............ A61F 7/03
　　　　　　　　　　　　　　　　　　　　607/108
2015/0297443 A1* 10/2015 Maurette ................ A61H 19/32
　　　　　　　　　　　　　　　　　　　　600/38

* cited by examiner

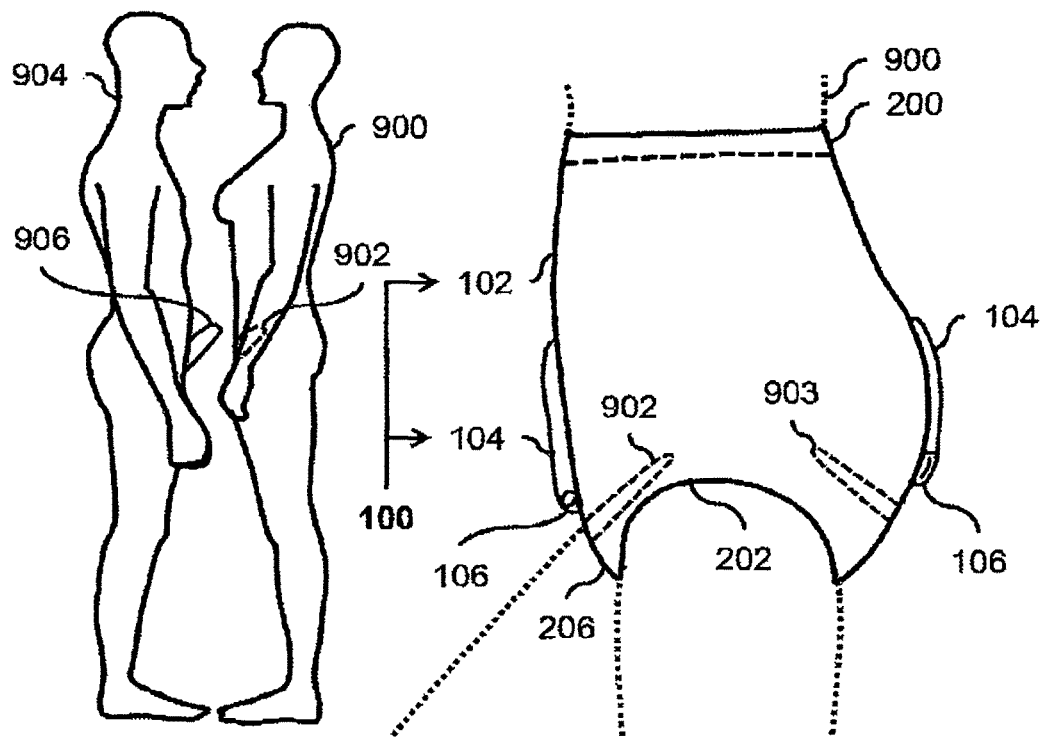

APPARATUS FOR SEXUAL ACTIVITY USAGE

CROSS-REFERENCE TO RELATED APPLICATIONS

I claim priority to my U.S. Provisional Patent Application 62/204,761, filed Aug. 13, 2015.

TECHNICAL FIELD OF THE INVENTION

The invention pertains to an apparatus for mimicked sexual activity usage between users. More specifically, the invention pertains to a garment worn by one user that allows entry of a body part of another user therein, providing sexual sensations and considerably reducing the risk of pregnancy and the occurrence of sexually transmitted infections as at no point either user enters the body of the other user.

BACKGROUND OF THE INVENTION

Unintended pregnancies are pregnancies that are mistimed, unplanned or unwanted at the time of conception. Unintended pregnancy mainly results from engaging in vaginal sexual activity without the use of contraception, or due to incorrect use of a contraceptive method, but may also arise from the failure of the contraception method when used correctly to prevent pregnancy. Available contraception methods include use of birth control pills, a condom, intrauterine device (IUD, IUC, IUS), contraceptive implant, hormonal patch, hormonal ring, cervical caps, diaphragms, spermicides, or sterilization. Women choose to use a contraceptive method based on method efficacy, medical considerations, side effects, convenience, availability, friends' or family members' experience, religious views, and many other factors. Some cultures limit or discourage access to birth control because they consider it to be morally or politically undesirable. Unintended pregnancies may also result from rape, incest or various other forms of forced or unwanted sex.

Sexually transmitted infections (STI), also referred to as sexually transmitted diseases (STD) and venereal diseases (VD), are infections that are commonly spread by sex, especially vaginal intercourse, anal sex and oral sex. Most STIs initially do not cause symptoms. This results in a greater risk of passing the disease on to others. Symptoms and signs of disease may include vaginal discharge, penile discharge, ulcers on or around the genitals, and pelvic pain. STIs acquired before or during birth may result in poor outcomes for the baby. Some STIs may cause problems with the ability to get pregnant. The most effective way of preventing STIs is by not having sex. In 2008, it was estimated that 500 million people were infected with either syphilis, gonorrhea, chlamydia or trichomoniasis. At least an additional 530 million people have genital herpes and 290 million women have human papillomavirus. STIs other than HIV resulted in 142,000 deaths in 2013. In the United States there were 19 million new cases of sexually transmitted infections in 2010. There is often shame and stigma associated with these infections. The term sexually transmitted infection is generally preferred over the terms sexually transmitted disease and venereal disease, as it includes those who do not have symptomatic disease.

U.S. Pat. No. 5,596,997 A discloses a female panty condom that has a panty that has an opening generally at the genital area of the wearer and is located approximately over the vagina of the wearer. The panty is a form of underwear worn by women and covers the genital area. A pouch includes a front side having a slit and a backside having a slit affixed to the panty. The slit in the front side of the pouch and the slit in the backside of the pouch are aligned. A sheath is positioned within the pouch behind the slit in the front side of the pouch such that the penis of a male partner may enter the opening of the sheath through the opening in the panty. The sheath will extend to cover the penis as it moves through the slit in the backside of the pouch and into the vagina of the wearer.

U.S. Patent 20130133665 A1 discloses a male or female full genital protective barrier garment device that has at least one inwardly or outwardly expandable and collapsible orifice covering for safe sex protection from body fluids, pathogens and parasites for a wearer and a partner which includes integral and multiple sensory, textural, visual and/or body enhancement components along with herbal, chemical and/or natural elements for increased stimulation in an undergarment device. The device includes a portion of the interior, and/or exterior surfaces of said male or female undergarment device have integral textural sensory sexual stimulant elements specifically positioned proximal to the wearer's, or partner's erogenous zones or other highly sensitive skin surface areas, which may include, but is not limited to the areas of a female person's "G-spot", "A-spot", "U-spot", clitoris, and anal area, and a male person's penis, scrotum, and anal area; to provide pleasure and stimulation to those areas. The underwear also allows for penetration of one or more body orifices by means of integral, permanently attached, liquid impermeable, inwardly or outwardly expandable and collapsible condom/sheath component element/s, which are closed at the distal end.

BRIEF SUMMARY OF INVENTION

It will be appreciated that there exists a need to mitigate (at least in part) at least one problem associated with the existing sex garments (also called the existing technology). After much study of the known systems and methods with experimentation, an understanding of the problem and its solution has been identified and is articulated as follows:

In accordance with U.S. Pat. No. 5,596,997 A (Inventor: Max M. ABADI, Publication date: 28 Jan. 1997) and UNITED STATES patent number 20130133665 A1 (Inventor: Anita Lynn Waller, Publication date: May 30, 2013), a sexual-activity garment (to be worn by a first user) provides a sexually-interactive opening assembly that is received in the body orifice of the second user. The sexually-interactive pouch assembly forms, an entryway configured to receive a body-extending member of a second user. Moreover, the body-extending member of the second user is permitted to extend into the body orifice of the first user because the sexually-interactive pouch assembly is received in the body orifice of the first user.

A problem associated with U.S. Pat. No. 5,596,997 and UNITED STATES patent number 20130133665 A1 is that for the case where the sexually-interactive pouch assembly breaks, the body orifice of the first user will come into direct contact with the body-extending member of the second user (causing the potential exchange of bodily fluid leading to disease and/or pregnancy). Under such circumstances, the bodily fluids of the first user and the second user may comingle and thereby may expose the first user and/or the second user to a sexual disease and/or pregnancy).

Therefore, what is needed is a device configured to further reduce the possibility of transfer of the sexually-transmittable disease and/or the chance of pregnancy for the first user and/or the second user. This would improve health, safety and/or birth control while permitting the possibility to conduct sexually-enjoyable activities (between people) with less concern for exchanging the sexually-transmittable fluid (s).

Another problem associated with U.S. Pat. No. 5,596,997 and UNITED STATES patent number 20130133665 A1 is that the devices do not take into account users who may want to engage in sexual relations one with another, but may want to abstain for a certain period of time. The sexually-interactive pouch worn by the first user enters the body orifice of the second user. This penetration constitutes the act of sexual intercourse.

Therefore, what is needed is a device configured to allow for a pleasurable, intimate sexual experience that mimics (mirrors) a body-extending member of a first person (a user) entering a body orifice of a second person (another user) without facilitating or allowing the actual act of penetration of the orifice of the second person with the body-extending member of the first person. This arrangement may allow for physical virginity and/or celibacy of either person to remain intact.

Another problem associated with U.S. Pat. No. 5,596,997 and UNITED STATES patent number 20130133665 A1 is that they do not take into account users who may want to engage in sexual relations one with another, but due to existing health, emotional or psychological conditions are unable to. The sexually-interactive pouch worn by the first user enters the body orifice of the second user. This may prove as uncomfortable or emotionally difficult for one or both users.

Therefore, what is needed is a device configured to allow for a pleasurable, intimate sexual experience that mimics (mirrors) a body-extending member of one person entering a body orifice of another person without the actual physical act of penetration. This arrangement may allow for reduced instance of physical discomfort, emotional or psychological strain.

Another problem associated with U.S. Pat. No. 5,596,997 and UNITED STATES patent number 20130133665 A1 is that the devices do not take into account users who may desire to engage in sexual relations by the penetration of a body extending member into the orifice of another while one user is experiencing menstruation (this may prove as messy or uncomfortable for either user).

Therefore, what is needed is a device configured to allow for a pleasurable, intimate sexual experience that mimics (mirrors) a body-extending member of one person entering a body orifice of another without the actual act of physical penetration, and thereby allow for reduced instance of discomfort or mess provided the wearer of the garment (the device) also wears a sanitary napkin or tampon over or inside of the vagina.

Another problem associated with U.S. Pat. No. 5,596,997 and UNITED STATES patent number 20130133665 A1 is that these devices do not take into account users who may desire to engage in sexual relations by the penetration of a body extending member into the orifice of another while one user is pregnant or one user may have recently given birth and may have been cautioned against allowing penetration of an orifice or may be uncomfortable allowing penetration into an orifice during or after pregnancy. This may result in a lack of intimacy between users (and may increase suspicion of or cause infidelity).

Therefore, what is needed is a device configured to allow for a pleasurable, intimate sexual experience that mimics (mirrors) a body-extending member of one person entering a body orifice of another without the actual act of penetration, thereby allowing for reduced instance of tearing vaginal stitches, vaginal pain, risking miscarriage in high-risk pregnancies and reducing the personal worry of a user who may fear harming the unborn baby.

To mitigate, at least in part, at least one problem associated with the existing technology, there is provided (in accordance with a major aspect) a garment that resolves the above problems (at least in part).

Other aspects are identified in the claims.

Other aspects and features of the non-limiting embodiments may now become apparent to those skilled in the art upon review of the following detailed description of the non-limiting embodiments with the accompanying drawings.

BRIEF DESCRIPTION OF THE DRAWINGS

The non-limiting embodiments may be more fully appreciated by reference to the following detailed description of the non-limiting embodiments when taken in conjunction with the accompanying drawings, in which:

FIG. 1 depicts a side view of a first user 900 and a second user 904;

FIG. 2 depicts a side view of an embodiment of an apparatus 100 for mimicked sexual activity usage between the users of FIG. 1;

Figure 3:
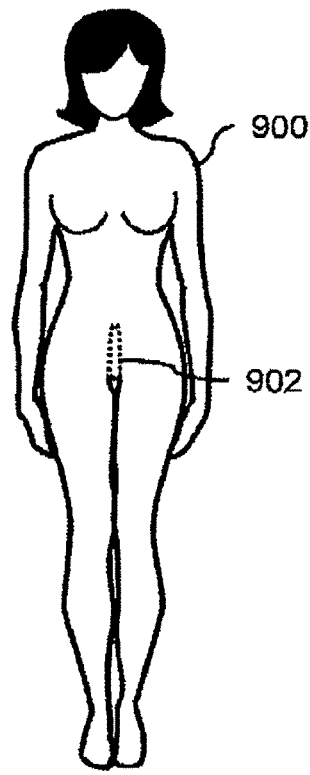
FIG. 3 depicts a front view of an embodiment of the first user 900 of FIG. 1.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted.

Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, but well-understood, elements that are useful or necessary in commercially feasible embodiments are often not depicted to provide a less obstructed view of the embodiments of the present disclosure.

LISTING OF REFERENCE NUMERALS USED IN THE DRAWINGS 100 apparatus
102 garment assembly
104 fluid-impenetrable receiver
106 entryway
108 textured interior portion
110 interior cavity
112 sexually-interactive textured material
114 flexible slit
116 heating element
118 vibrating element
120 heater device
122 vibrator device
200 control section
202 first body part opening
204 second body part opening
206 genital covering portion
208 suction element
300 testicle stimulator
302 linking device
900 first user
902 body orifice
903 anal area
904 second user
906 body-extending member

DETAILED DESCRIPTION OF THE INVENTION

The following detailed description is merely exemplary and is not intended to limit the described embodiments of the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the invention is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field of the Invention, Background of the Invention, Summary of the Invention or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the invention is limited to the subject matter provided by the claims, and that the invention is not limited to the particular aspects depicted and described.

FIG. 1 depicts a side view of a first user 900 and a second user 904.

In general terms, the first user 900 has a body orifice 902. The second user 904 has a body-extending member 906.

Figure 5:
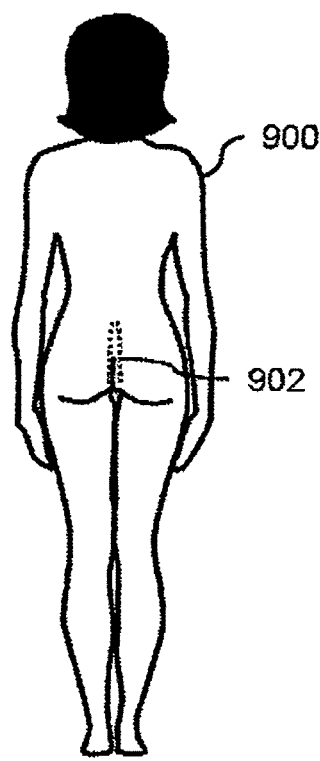
FIG. 5 depicts a rear view of an embodiment of the first user 900 of FIG. 1.

In accordance with the embodiment as depicted in FIG. 1, the first user 900 includes (is) a female (a woman) with the body orifice 902 including either the vagina (as depicted in FIG. 1 and FIG. 3) or the anal canal (the anus) as depicted in FIG. 5. The second user 904 includes (is) a male (a man) with the body-extending member 906 including the penis.

In accordance with another embodiment, the first user 900 includes (is) a female (a woman) and the second user 904 includes (is) also a female (a woman). For this case, the body-extending member 906 includes a strap-on device (as a substitute for the penis of a man). It will be appreciated that one of the women wears and uses the strap-on device. The strap-on device is a dildo attached to a belt, and may be worn tied around the waist (of the user). The strap-on device may be used to vaginally or anally penetrate a woman (for instance, by another woman or a man). The strap-on device may be used to anally penetrate a man (for instance, by woman or by another man).

In accordance with another embodiment, the first user 900 includes (is) a male (a man), in which the body orifice 902 includes the anal canal. The second user 904 includes (is) also a male (a man), in which the body-extending member 906 includes the penis (or the strap-on device).

FIG. 2 depicts a side view of an embodiment of an apparatus 100 for mimicked sexual activity usage between the users of FIG. 1.

In accordance with a general embodiment, there is provided an apparatus 100. The apparatus 100 is used (to be worn by a user) and is for mitigating (preferably, preventing) the transfer of a sexually-transmittable fluid (between the first user 900 and the second user 904). The transfer of the sexually-transmittable fluid may cause an unwanted disease and/or an unwanted pregnancy (as the case may be). The first user 900 and the second user 904 desire to avoid such unwanted scenarios. The apparatus 100 provides an advantage (technical effect) of reducing (preferably eliminating) the possibility of transfer of the sexually-transmittable fluid related to infection, disease and/or the chance of an unwanted pregnancy (for any one of the first user 900 and the second user 904).

Another technical effect is that the apparatus 100 is that the apparatus 100 allows the first user 900 and the second user 904 to mimic the motion and/or the sensation of sexual intercourse without the penetration of the body-extending member 906 of the second user 904 into the body orifice 902 of the body of the first user 900. In this manner, unwanted disease and/or unwanted pregnancy may be avoided while permitting augmented (mimicked) sexual activity between the users.

Preferably, the apparatus 100 allows for the second user 904 to insert the body-extending member 906 into a fluid-impenetrable receiver 104 worn by the first user 900 rather than into the a body orifice of the first user 900. This action will mimic conventional sexual intercourse without the penetration of a body-extending member into a body orifice. Examples of body-extending members include but are not restricted to a penis, a tongue and a finger. Examples of a body-orifice include but are not restricted to a vagina, an anus and a mouth. As the body-extending member 906 of the second user 904 penetrates the fluid-impenetrable receiver affixed to the garment assembly 102 of the apparatus 100, a textured interior portion 108 located proximate to the crotch area of the garment assembly is in contact with the genital area of the first user 900. The fluid-impenetrable receiver 104 is lined with sexually-interactive textured material 112 and has a goal of pleasuring the second user 904 in the same way as the textured interior position 108 has a goal of pleasuring the first under 902 as the body-extending member 906 moves inside the fluid-impenetrable receiver 104.

In accordance with the embodiment as depicted in FIG. 2, the apparatus 100 is to be worn by the first user 900 having the body orifice 902 while the first user 900 engages in augmented sexual activity with the second user 904 (depicted in FIG. 1) having the body-extending member 906.

The apparatus 100 includes (and is not limited to) a synergistic combination of a garment assembly 102 and a fluid-impenetrable receiver 104.

More specifically, the garment assembly 102 (also called a panel section) is configured to be worn by the first user 900 relative to the body orifice 902 of the first user 900 (preferably while the first user 900 and the second user 904 engage in mimicked sexual activity with each other).

The garment assembly 102 may include a fabric material configured to be skin compatible with the skin of the first user 900 who is to wear the garment assembly 102 and may contact the interior of the apparatus 100 (that is, to avoid harm to the skin of the user, such as an allergic reaction, etc.). In addition, the garment assembly 102 may include the fabric material configured to be skin compatible with the skin of the second user 904 who may come into physical contact with the exterior of the garment assembly 102.

In accordance with a preferred option, the garment assembly 102 includes a fluid-impenetrable material. It will be appreciated that the garment assembly 102 may include any type of the fabric material (that is skin compatible), such as a woven fabric material, a nonwoven fabric material, a knitted fabric, a latex material (natural or synthetic), silicone, an elastane material, a rubber material (natural or artificial), a leather material (natural or artificial), and any equivalent thereof. The woven fabric stretches diagonally on the bias directions (between the warp and weft directions), unless the threads used are elastic. Woven fabric cloth usually frays at the edges, unless techniques are used to counter it, such as the use of pinking shears or hemming. The nonwoven fabric is a fabric-like material made from long fibers, bonded together by chemical, mechanical, heat or solvent treatment, such as felt, which are neither woven nor knitted. Some nonwoven materials lack sufficient strength unless densified or reinforced by a backing. The knitted fabric is a textile that results from knitting, and has properties that are distinct from woven fabric in that the knitted fabric is more flexible. The latex material includes a stable dispersion (emulsion) of polymer microparticles in an aqueous medium. Latex itself is natural, and synthetic latexes have been made. Synthetic latexes may be made by polymerizing a monomer such as styrene that has been emulsified with surfactants. The elastane material (also known as the Spandex material or the Lycra material) is a synthetic fiber known for its exceptional elasticity. It is stronger and more durable than natural rubber (the elastane material is a polyester-polyurethane copolymer). The rubber material may include a natural rubber consists of polymers of the organic compound isoprene, with minor impurities of other organic compounds plus water. Forms of polyisoprene that are used as natural rubbers are classified as elastomers.

The garment assembly 102 may be manufactured in a conventional manner with conventional knitted fabric materials such as nylon, the LYCRA (TRADEMARK) material, the SPANDEX (TRADEMARK) material, translucent material, silk, vegan material, sheepskin, nitrile, vinyl, viscose, cellulose, cotton, etc. For instance, the garment assembly 102 may be manufactured on a circular hosiery-knitting machine using a circular knitting process (or any equivalent thereof). It will be appreciated that those skilled in the art of manufacturing garments will understand the manner in which to manufacture the garment assembly 102 and to attach the fluid-impenetrable receiver 104 to the garment assembly 102.

In accordance with an option of the embodiment as depicted in FIG. 2, the garment assembly 102 may be manufactured in one solid piece where the fluid-impenetrable receiver 104 cannot be attached or detached. For instance, one continuous fluid impenetrable fabric is used for the entire garment 102 and the fluid-impenetrable receiver 104. It will be appreciated that those skilled in the art of manufacturing garments will understand the manner in which to manufacture the garment assembly 102 to include the fluid-impenetrable receiver 104 to the garment assembly 102.

In accordance with the embodiment as depicted in FIG. 2, the garment assembly 102 includes a control section 200 (also called a control top). The control section 200 is configured to facilitate a snug fit of the garment assembly 102 to the skin of the first user 900. For instance, the control section 200 may be configured to surround the waist section of the first user 900, and to snug fit the garment assembly 102 to the waist section of the first user 900 (this is done in such a way that the garment assembly 102 remains securely fitted to the waist of the first user 900 during mimicked sexual activity between the users). The control section 200 may be called a form-fitting flexible garment portion, etc.

In accordance with the embodiment as depicted in FIG. 2, the garment assembly 102 includes (defines) a first body part opening 202 (also called a first leg opening) and a second body part opening 204 (also called a second leg opening). The first body part opening 202 is spaced apart from the second body part opening 204, and is positioned adjacent thereto. In accordance with a preferred option, the first body part opening 202 and the second body part opening 204 includes a control portion configured to securely fit the first body part opening 202 and the second body part opening 204 to the skin or body of the first user 900 (such as at the first leg and the second leg, respectively).

Figure 8:
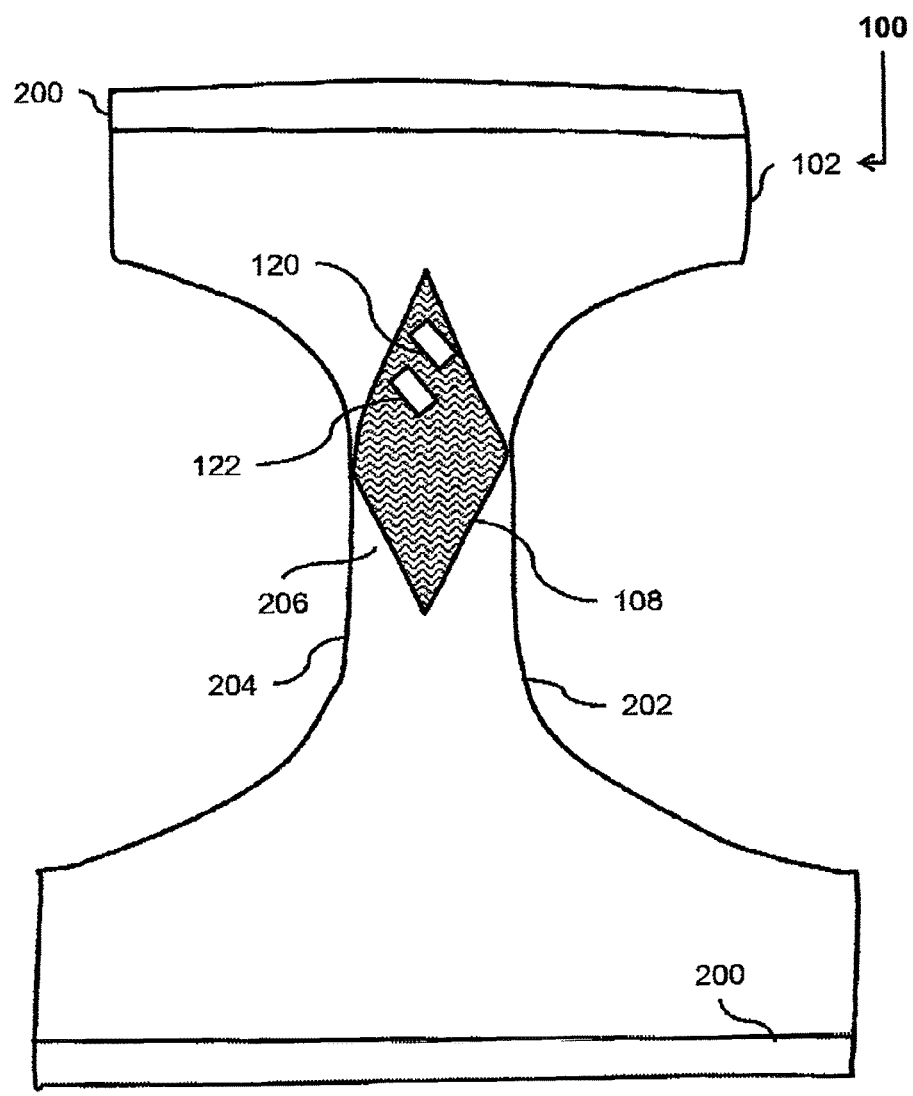
FIG. 8 depicts an interior view of an embodiment of the apparatus 100 of FIG. 2.

In accordance with the embodiment as depicted in FIG. 2, the garment assembly 102 includes a genital covering portion 206 configured to be positioned proximate to (preferably, to cover at least in part) the genital area of the first user 900 and/or to cover the anal area of the first user 900. As seen in FIGS. 2 and 8, similar to traditional underwear, the garment assembly includes a front panel portion located at one end of the genital covering portion for covering a lower abdomen of the first user and a back panel portion at an end of the genital covering opposite to the front panel portion for covering buttocks of the first user.

Figure 11:
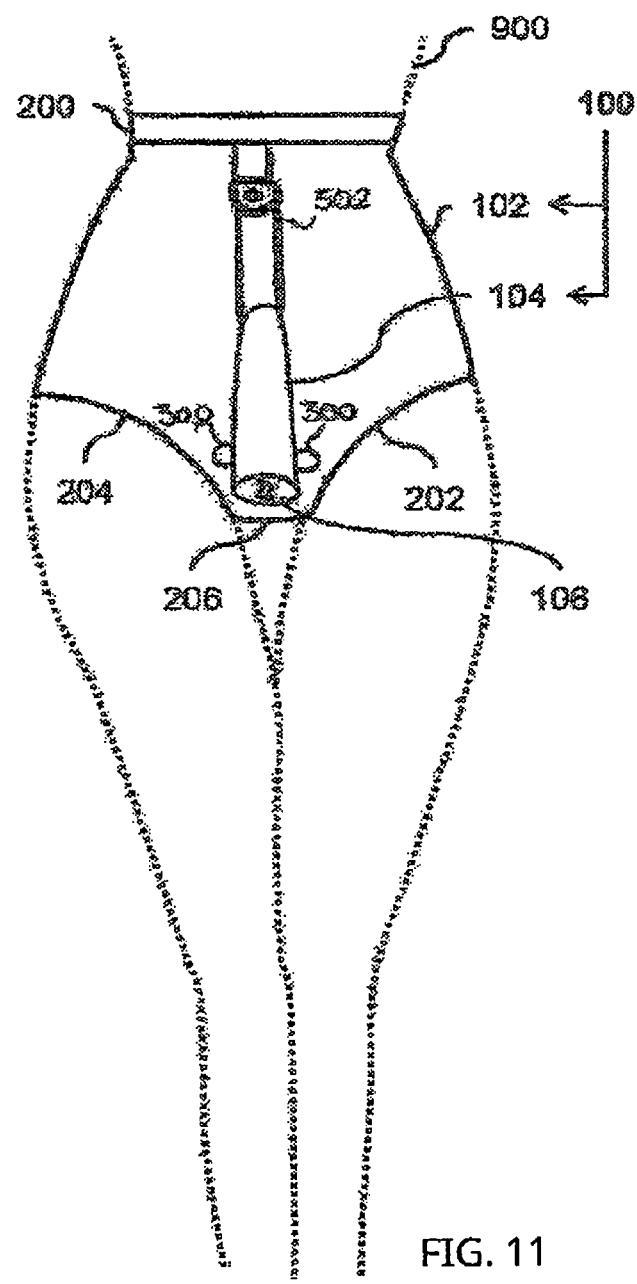
FIG. 11 depicts a front view of a modified form of construction of an embodiment of the apparatus 100 of FIG. 10.

In accordance with the embodiment as depicted in FIG. 11, the garment assembly 102 includes a linking device 302, comprised of wire, ribbon, string, plastic, rubber, silicone or similar material and a wheel, a spoke, or similar other material proximate to the fluid-impenetrable receiver 104 and the textured interior portion 108, having the motion of a pulley wherein it allows for movement experienced as a result of the body-extending member 906 of the second user 904 to trigger movement of the textured interior portion 108 of the garment assembly 102 worn by the first user 900.

Figure 9:
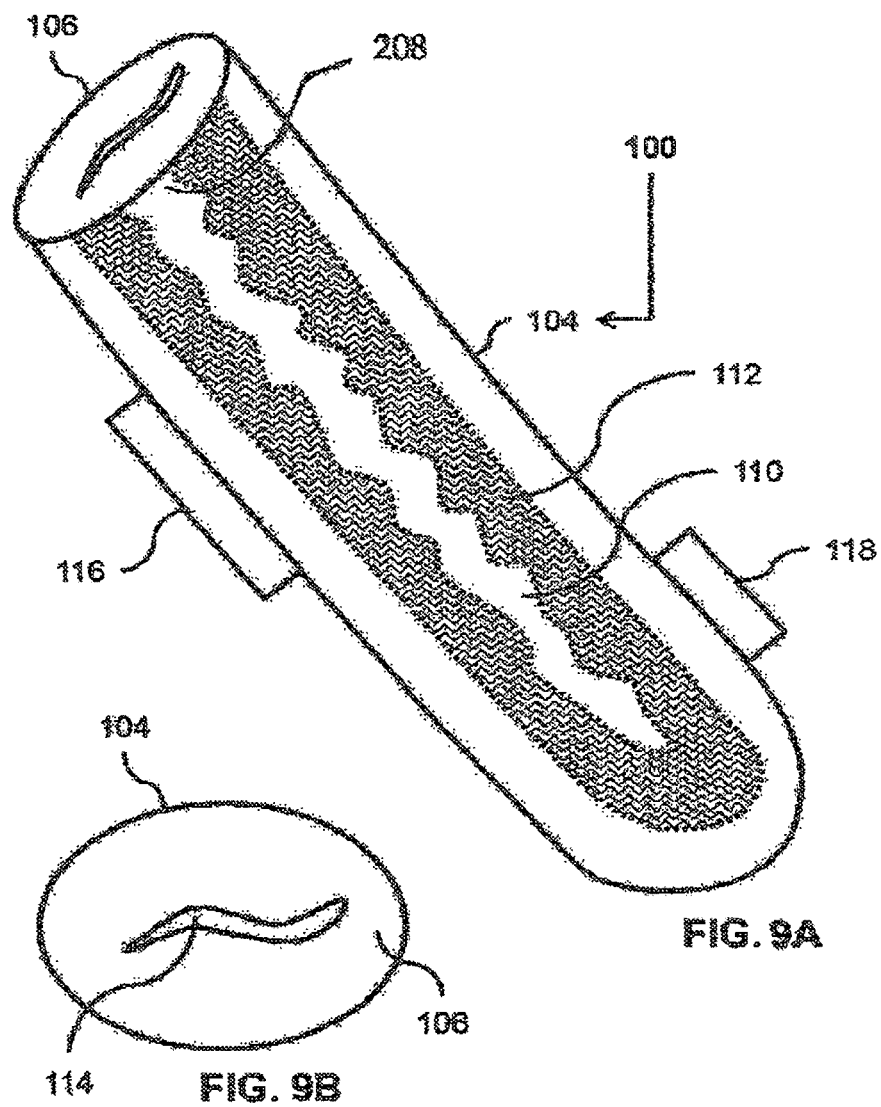
FIG. 9A depicts a sectional view of an embodiment of a fluid-impenetrable receiver 104 of the apparatus 100 of FIG. 2.
FIG. 9B depicts an end view of an embodiment of an entry way 106 of the fluid-impenetrable receiver 104 FIG. 9 A.
Figure 10:
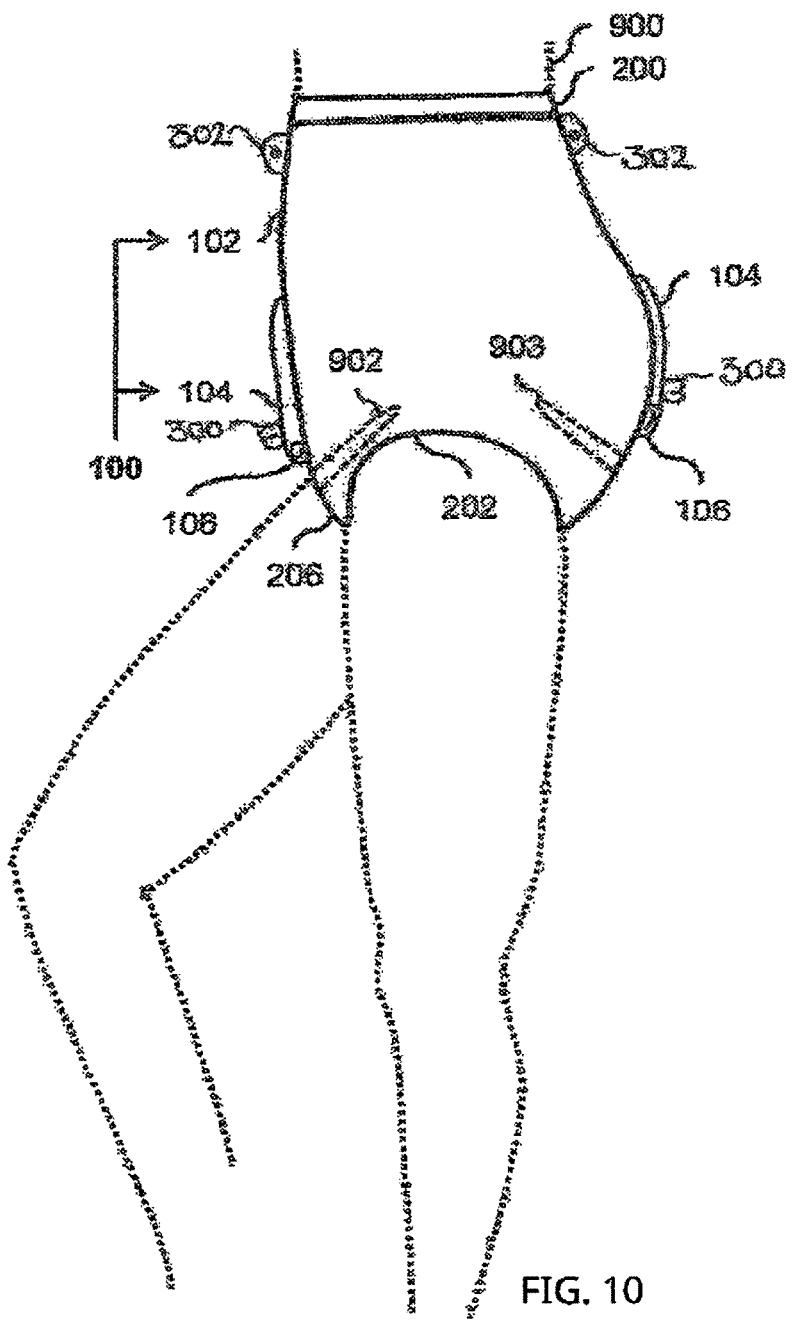
FIG. 10 depicts a side view of a modified form of construction of an embodiment of an apparatus 100 for mimicked sexual activity usage between the users of FIG. 1.

In accordance with an embodiment as depicted in FIG. 9A, the interior cavity 110 of the fluid-impenetrable receiver 104 is configured to have a suction capability. More specifically, providing a suction element 208 in such that the body-extending member of the second user 904 experiences a suction sensation inside the fluid-impenetrable receiver 104.

In accordance with a preferred embodiment, the fluid-impenetrable receiver 104 may include a fluid-impenetrable material. The fluid-impenetrable receiver 104 may be called a pouch having a pouch entrance, or a pouch barrier assembly (and any equivalent thereof). The fluid-impenetrable receiver 104 may include any type of fluid-impenetrable material, such as a latex material (natural or synthetic), polyurethane, nitrile, vinyl, sheepskin, cellulose, plastic, spandex, cotton, cloth, rayon, nylon, viscose, vegan substance, silicone, a rubber material (natural or artificial), and any equivalent thereof. Preferably, the fluid-impenetrable receiver 104 is skin compatible with the first user 900 and with the second user 904.

In accordance with an embodiment, the fluid-impenetrable receiver 104 is configured to (in use) (A) expand (elastically deform or elastically stretch), as necessary, to receive and house (conformably receive) the body-extending member of second user 904, and (B) elastically contract in response withdrawal of the body-extending member of second user 904 from the fluid-impenetrable receiver 104. This feature may have the advantage of allowing the second user 904 to feel more pleasure during the mimicked sexual act (between the users).

The fluid-impenetrable receiver 104 and the garment assembly 102 are fixedly coupled (thermally bonded, chemically bonded, glued, physically connected, buttoned, zippered, clamped, strung, ribbed, stitched) together. This is done in such a way that the fluid-impenetrable receiver 104 is securely affixed to the garment assembly 102. Preferably, during mimicked sexual activity (between the first user 900 and the second user 904), the bond (affixed connection) between the garment assembly 102 and the fluid-impenetrable receiver 104 is configured to withstand inadvertent breakage.

The fluid-impenetrable receiver 104 is configured to form, at least in part, an entryway 106 configured to operatively receive, at least in part, the body-extending member 906 of the second user 904. If required, a lubrication fluid may be applied to the fluid-impenetrable receiver 104 and/or to the body-extending member 906 (in order to facilitate a relatively easier insertion of the body-extending member 906 into and out from the fluid-impenetrable receiver 104. Preferably, the fluid-impenetrable receiver 104 is chemically compatible with the lubrication fluid (for this case).

In addition, the fluid-impenetrable receiver 104 is also configured to be affixed to the garment assembly 102 at a fixed position and fixed orientation relative to the body-extending member 906. The fluid-impenetrable receiver 104 is also configured to be spaced apart from and be positioned and remain entirely outside of the body orifice 902 of the first user 900 once the first user 900 wears the garment assembly 102. This is done in such a way that transfer of a sexually-transmittable fluid between the first user 900 and the second user 904 is reduced (and is preferably avoided altogether for best results).

In accordance with an embodiment, there is provided at least one or more instances of the fluid-impenetrable receiver 104 positioned on the garment assembly 102 in a spaced-apart arrangement relative to each other. As depicted in FIG. 2 there are two instances of the fluid-impenetrable receiver 104 fixedly attached to the garment assembly 102.

In accordance with an embodiment, the garment assembly 102 includes a thong, a g-string, a panty, a brief, pants, trousers, a shirt, and any garment that covers any body part of the user (the wearer of the garment assembly 102) and any equivalent thereof.

A technical effect is that the apparatus 100 mitigates or reduces, at least in part, (preferably, prevents altogether) the transfer of the sexually-transmittable fluid between the first user 900 and the second user 904. An advantage of the apparatus 100 is the reduction of transmission of sexually-transmittable diseases between the first user 900 and the second user 904 and/or unwanted pregnancy.

In accordance with an embodiment, the snug fit of the garment assembly 102 (to the first user 900) is configured to allow for the fluid-impenetrable receiver 104 to remain secured to the garment assembly 102 (preferably during mimicked sexual activity between the users). A relatively slight level of elasticity in the fluid-impenetrable receiver 104 and in the garment assembly 102 is configured to allow for relative ease of movement as the body-extending member 906 moves inside and out from the fluid-impenetrable receiver 104 while the bodies of the first user 900 an the second user 904 are in the motion of mimicked sexual activity (mimicked motion of sexual activity).

In accordance with a preferred option, the penetration of the body-extending member 906 of the second user 904 is limited to penetrating the fluid-impenetrable receiver 104 rather than penetrating the body orifice 902 of the first user 900.

In accordance with more specific options, the fluid-impenetrable receiver 104 is further configured to be affixed to the garment assembly 102 at a fixed position and fixed orientation relative to the body-extending member 906. This is done in such a way that once the body-extending member 906 of the second user 904 is slidably reciprocated into and out from the fluid-impenetrable receiver 104 via the entryway 106, the fluid-impenetrable receiver 104 remains in the fixed position and the fixed orientation relative to the garment assembly 102. More specifically, the fluid-impenetrable receiver 104 may be fixedly attached to the garment assembly 102 along a length of the fluid-impenetrable receiver 104 (or along the entire length of the fluid-impenetrable receiver 104).

In accordance with an option, the fluid-impenetrable receiver 104 is thermally bonded or chemically bonded (using a flexible adhesive) to the garment assembly 102 (depending on the type of materials involved). For instance, polyurethane glues remain somewhat flexible (once set and hardened) in such a way that the cured adhesive does not crack off (delaminate) from the fluid-impenetrable receiver 104 and/or the garment assembly 102. For instance, contact cement adhesive (the water soluble version should be avoided, and the solvent soluble version is preferred). A latex glue may be used (for the case where the fluid-impenetrable receiver 104 and the garment assembly 102 each includes latex. Rubber cements are usually thinned with heptane (a thinning agent). The thinning agent is used to prepare surfaces (of latex) for gluing with the rubber cement. For instance, a good way to apply the glue to a latex sheet is to use a piece of stiff plastic and spread the glue out on both surfaces. Let the glue dry for about 15 minutes and then attach the two latex surfaces together. Apply a roller over the seam (to finish the seam). Wait for the seam to cure for about 24 hours before putting stress on the glued area.

In accordance with a preferred option, the fluid-impenetrable receiver 104 is further configured to be spaced apart from and be positioned and remain entirely outside of the body orifice 902 of the first user 900 once the first user 900 wears the garment assembly 102. This is done in such a way that flow of a sexually-transmittable fluid between the first user 900 and the second user 904 is reduced, at least in part, once the body-extending member 906 of the second user 904 is received into and breaks the fluid-impenetrable receiver 104 while the first user 900 wears the garment assembly 102 (with the fluid-impenetrable receiver 104 receiving, at least in part, the body-extending member 906 of the second user 904 and with the fluid-impenetrable receiver 104 remaining entirely outside of the body orifice 902 of the first user 900).

In accordance with the embodiment as depicted in FIG. 2, the fluid-impenetrable receiver 104 is spatially positioned on (such as, on the exterior surface of) the garment assembly 102 at a position that is located proximate to the body orifice 902 of the first user 900.

In accordance with an option, the fluid-impenetrable receiver 104 is spatially positioned on a lower section of the garment assembly 102 at a position that is located proximate to the body orifice 902 of the first user 900.

In accordance with the embodiment as depicted in FIG. 2, the apparatus 100 includes two instances of the fluid-impenetrable receiver 104. One instance of the fluid-impenetrable receiver 104 is positioned proximate to (such as, over) the genital area of the first user 900. Another instance of the fluid-impenetrable receiver 104 is positioned (mounted) proximate to (such as, over) the anal area 903 of the first user 900.

FIG. 3 depicts a front view of an embodiment of the first user 900 of FIG. 1. In accordance with the embodiment as depicted in FIG. 3, the first user 900 is a woman.

Figure 4:
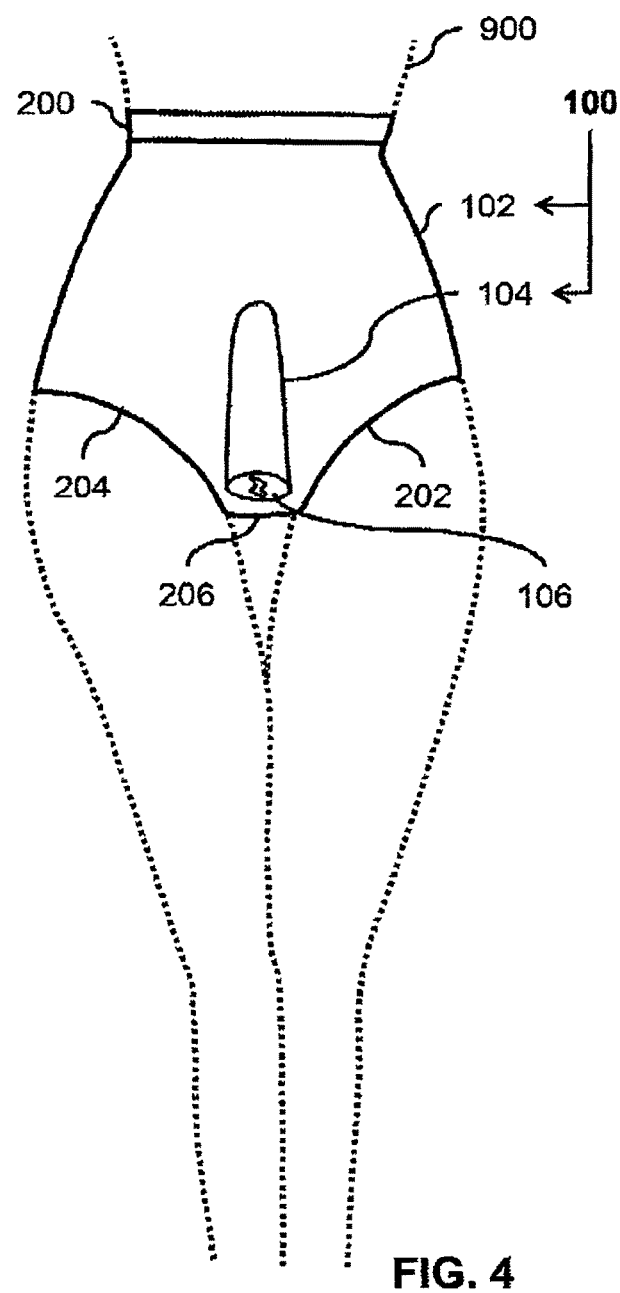
FIG. 4 depicts a front view of an embodiment of the apparatus 100 of FIG. 2.

FIG. 4 depicts a front view of an embodiment of the apparatus 100 of FIG. 2.

In accordance with the embodiment as depicted in FIG. 3, the garment assembly 102 is configured to be worn, at least in part, proximate to (such as, over) the genital area of the first user 900. The fluid-impenetrable receiver 104 is positioned proximate to (such as, over) the genital area of the first user 900.

Figure 15:
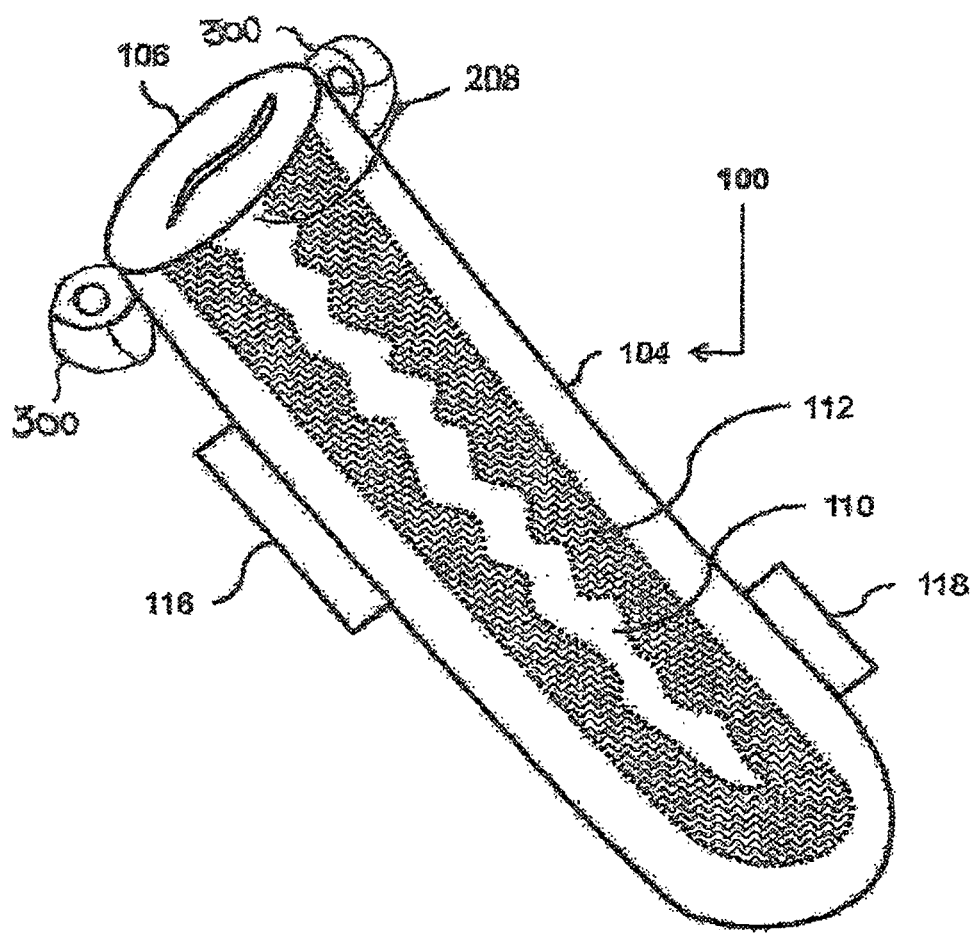
FIG. 15 depicts a sectional view of a modified form of an embodiment of a fluid-impenetrable receiver 104 of the apparatus 100 of FIG. 10.

In accordance with an embodiment as depicted in FIG. 15, testicle stimulator 300 which may be comprised of a sack, ball, sphere or any combination thereof filled with deformable material for allowing the sack to take on any curvature designed to have contact with, massage, tickle, heat, vibrate, caress or to provide any degree of added pleasure and or delight to the testicle area, gonad area, scrotum area or any combination thereof, of the second user is fixed proximate to the fluid-impenetrable receiver 104 proximate to the garment assembly 102 by heat, sewing, stitching, fusion or any other means of bringing the testicle stimulator and the fluid-impenetrable receiver 104 together.

Figure 12:
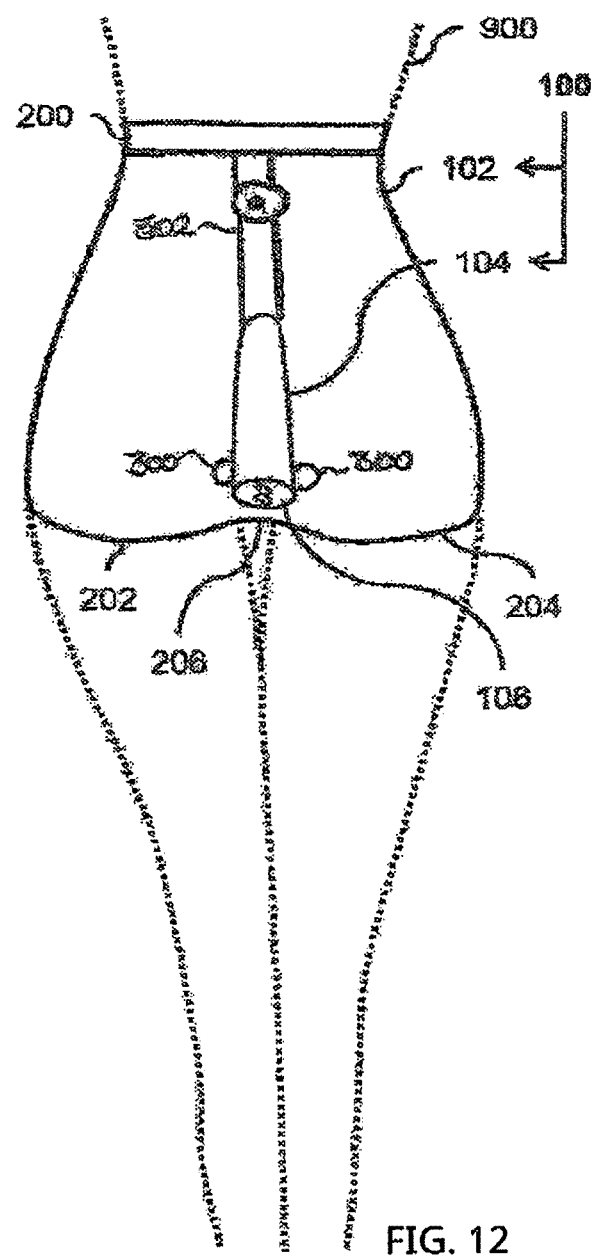
FIG. 12 depicts a rear view of a modified form of construction of an embodiment of the apparatus 100 of FIG. 10.
Figure 13:
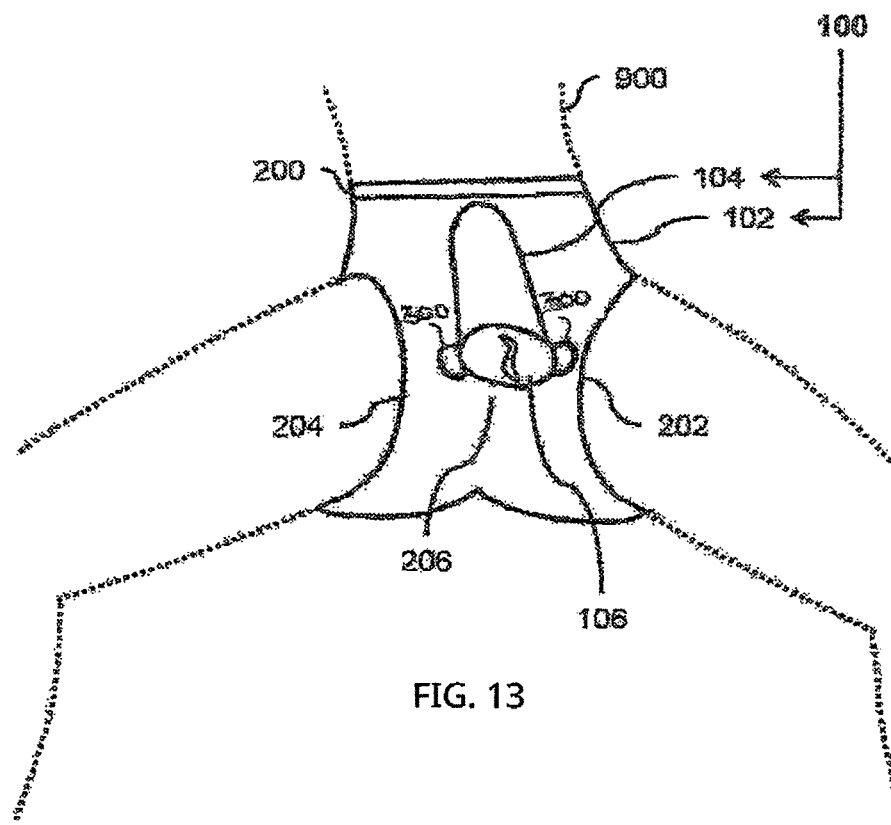
FIG. 13 depicts a front view of a modified form of construction of an embodiment of the apparatus 100 of FIG. 10.
Figure 14:
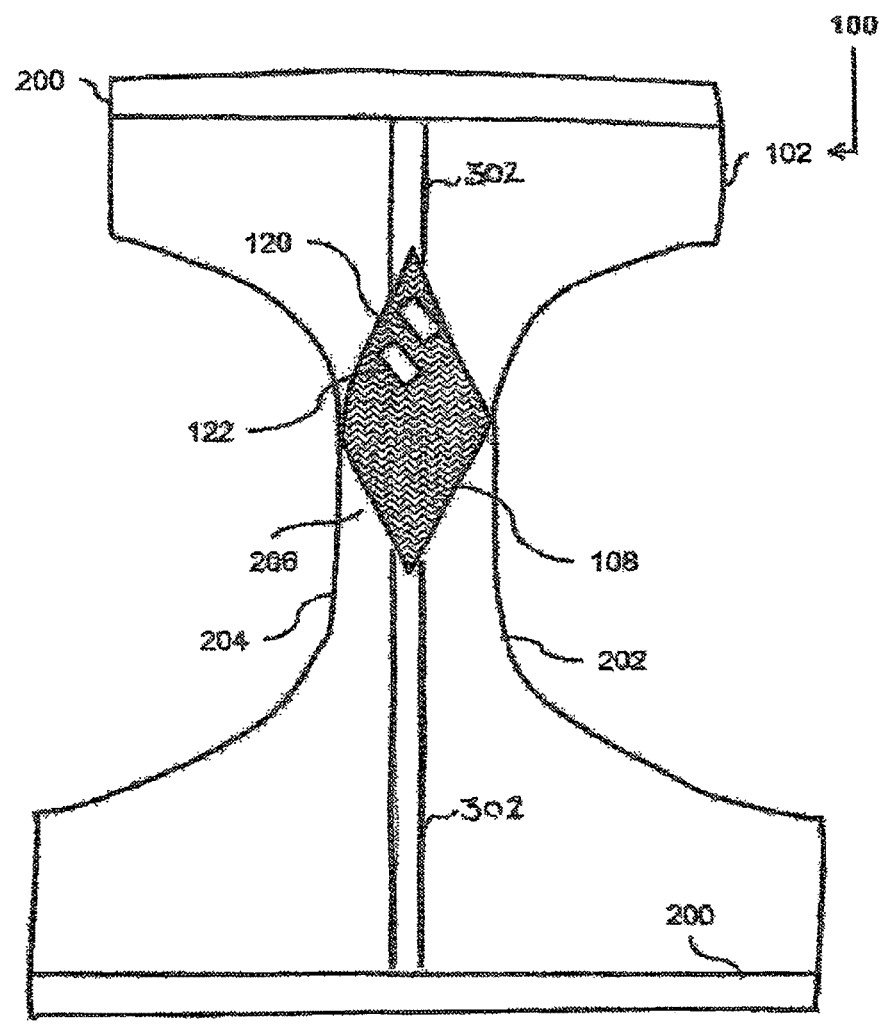
FIG. 14 depicts an interior view of a modified form of construction of an embodiment of the apparatus 100 of FIG. 10.

In accordance with an embodiment as depicted in FIG. 12, testicle stimulator 300 which may be comprised of a sack, ball, sphere or any combination thereof filled with deformable material for allowing the sack to take on any curvature designed to have contact with, massage, tickle, heat, vibrate, caress or to provide any degree of pleasure and or delight to the testicle area, gonad area, scrotum area or any combination thereof, of the second user is fixed proximate to the garment assembly 102 proximate to the fluid-impenetrable receiver 104 by heat, sewing, stitching, fusion or any other means of bringing the fluid-impenetrable receiver 104 and the testicle stimulator 300 together.

FIG. 5 depicts a rear view of an embodiment of the first user 900 of FIG. 1. In accordance with the embodiment as depicted in FIG. 4, the first user 900 is a woman.

Figure 6:
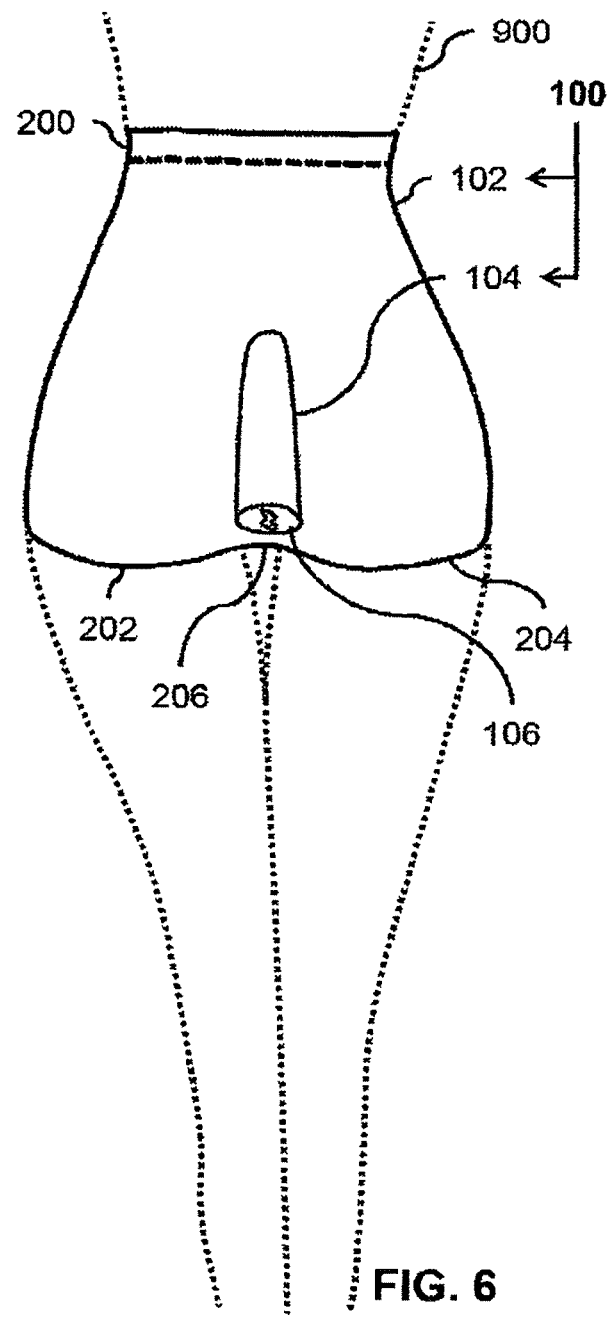
FIG. 6 depicts a rear view of an embodiment of the apparatus 100 of FIG. 2.

FIG. 6 depicts a rear view of an embodiment of the apparatus 100 of FIG. 2.

In accordance with the embodiment as depicted in FIG. 6, the fluid-impenetrable receiver 104 is positioned (mounted) proximate to (such as, over) the anal area of the first user 900.

Figure 7:
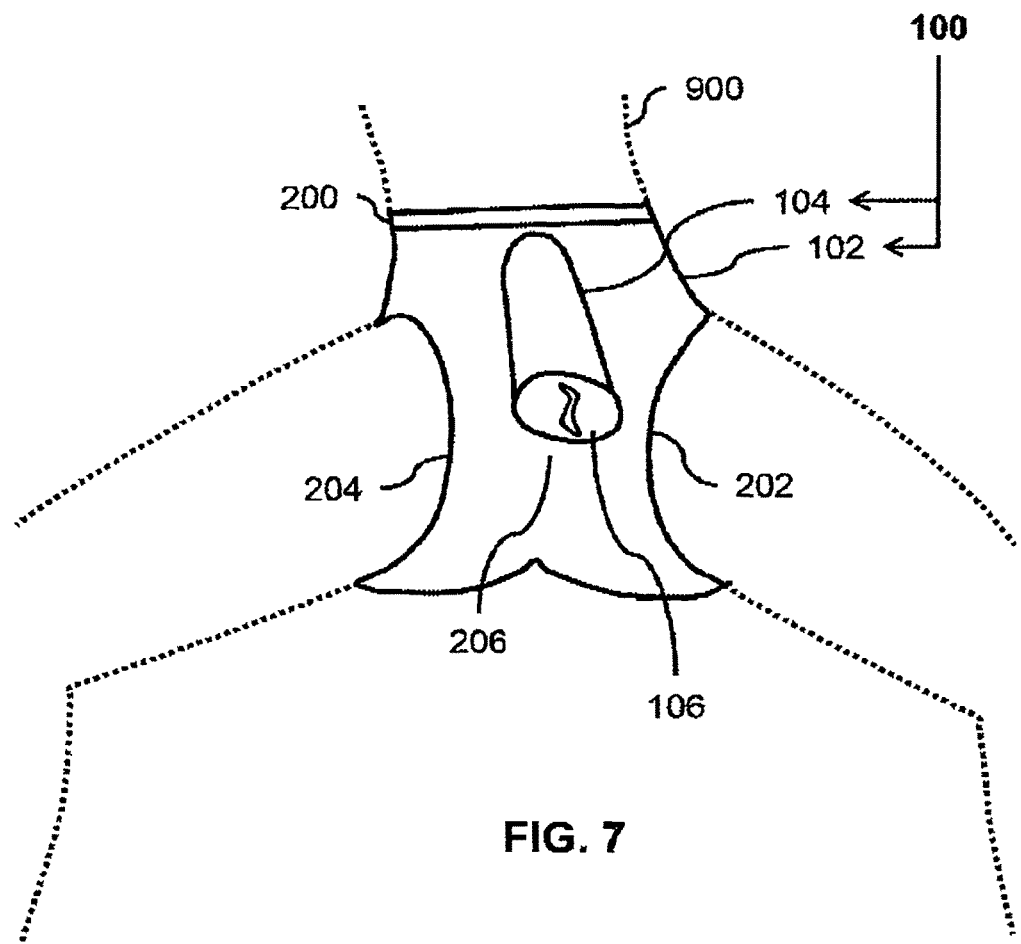
FIG. 7 depicts a front view of an embodiment of the apparatus 100 of FIG. 2.

FIG. 7 depicts a front view of an embodiment of the apparatus 100 of FIG. 2.

In accordance with the embodiment as depicted in FIG. 7, the apparatus 100 is worn by the first user 900, in which the first user 900 is depicted as partially laying down on his or her back. The fluid-impenetrable receiver 104 is affixed to a frontal section of the garment assembly 102.

FIG. 8 depicts an interior view of an embodiment of the apparatus 100 of FIG. 2.

In accordance with the embodiment as depicted in FIG. 8, the garment assembly 102 is configured to be worn over the genital area of the first user 900 (depicted in FIG. 1). The garment assembly 102 includes a textured interior portion 108 configured to face the genital area of the first user 900. The textured interior portion 108 is configured to assist in providing sexual pleasure to the first user 900 during mimicked sexual activity between the first user 900 and the second user 904 (to the sexual advantage of the first user 900).

In accordance with an embodiment, the garment assembly 102 includes the textured interior portion 108 extending to along (at least in part) a length (preferably along a complete length) and/or a width (preferably along a complete width) of the interior portion of the garment assembly 102. The textured interior portion 108 may be configured to (A) face the genital area of the first user 900, (B) face the genital area of the first user 900 and face the skin of the first user 900, (C) face the genital area of the first user 900 and face the skin of the first user 900 and face the skin of the first user 900.

The textured interior portion 108 may be called a liner or a textured gusset. The textured interior portion 108 is affixed to the interior of the garment assembly 102. This is done in such a way that the textured interior portion 108 may have physical contact with the genital area of the first user 900 (once the first user 900 wears the apparatus 100 just so). Of course, a lubricant fluid may be applied to the textured interior portion 108 before the garment assembly 102 is worn by the first user 900 (if so desired). The textured interior portion 108 is skin compatible with the skin of the first user 900 and is also compatible with the lubrication fluid.

The textured interior portion 108 includes (for instance) a ribbed section, a beaded section, a raised section, textured section (and any equivalent thereof). The textured interior portion 108 is configured to stimulate the first user 900 (once the first user 900 wears the garment assembly 102 just so) during the time the body-extending member 906 is moving into and out from the fluid-impenetrable receiver 104 (depicted in FIG. 7), depending on the sexual position taken (assumed) between the first user 900 and the second user 904 (depicted in FIG. 1). The textured interior portion 108 found at the interior of the garment assembly 102 is configured to contact (touch) the genital area of the first user 900 in such a way that the textured interior portion 108 provides (in use) sexual stimulation for the first user 900 as the body-extending member 906 of the second user 904 moves inside the fluid-impenetrable receiver 104.

In accordance with an embodiment, the textured interior portion 108 includes a heater device 120 configured to (in use) provide heat to the textured interior portion 108. This is done in such a way that the textured interior portion 108 receives the heat and spreads the heat that was received from the heater device 120 to a portion of the user wearing the textured interior portion 108.

In accordance with an embodiment, the textured interior portion 108 includes a vibrator device 122 configured to (in use) provide vibration motion to the textured interior portion 108. This is done in such a way that the textured interior portion 108 receives the vibration motion and spreads the vibration motion that was received from the vibrator device 122 to a portion of the user wearing the textured interior portion 108.

FIG. 9A depicts a side view of an embodiment of the fluid-impenetrable receiver 104 of the apparatus 100 of FIG. 2.

In accordance with FIG. 9A, there is depicted an interior view of the fluid-impenetrable receiver 104. In accordance with the embodiment as depicted in FIG. 9A, the fluid-impenetrable receiver 104 defines an interior cavity 110 configured to receive, at least in part, the body-extending member 906 of the second user 904 (depicted in FIG. 1). A sexually-interactive textured material 112 is configured to contact, at least in part, the body-extending member 906 of the second user 904 (once the body-extending member 906 of the second user 904 is received in the fluid-impenetrable receiver 104 just so). For instance, the sexually-interactive textured material 112 may include (and is not restricted) to a thermally activated material with an elastomeric gel material.

In accordance with an embodiment, the garment assembly 102 includes the fluid-impenetrable receiver 104 and the sexually-interactive textured material 112 extending to along (at least in part) a length (preferably along a complete length) and/or along a width of the garment assembly 102.

In accordance with an embodiment, the interior cavity 110 of the fluid-impenetrable receiver 104 is configured to be heatable. More specifically, a heating element 116 is positioned proximate to (operatively coupled to) the fluid-impenetrable receiver 104 (along a length and/or a width thereof) in such a way that the fluid-impenetrable receiver 104 receives (in use) heat from the heating element 116.

In accordance with an embodiment, the interior cavity 110 of the fluid-impenetrable receiver 104 is configured to be vibrated. More specifically, a vibrating element 118 is positioned proximate to (operatively coupled to) the fluid-impenetrable receiver 104 (along a length and/or a width thereof) in such a way that the fluid-impenetrable receiver 104 receives (in use) vibration motion from the vibrating element 118.

A lubricant fluid may be applied to the interior cavity 110 (if so desired) for the sexual pleasure of the second user 904. The fluid-impenetrable receiver 104 with the sexually-interactive textured material 112 (also called a textured portion) is configured to provide the second user 904 with the body-extending member 906 added (improved) pleasure as the second user 904 moves (reciprocates) the body-extending member 906 inside and outside of the fluid-impenetrable receiver 104. The fluid-impenetrable receiver 104 with the sexually-interactive textured material 112 positioned in the interior of the fluid-impenetrable receiver 104 may give (provide) the second user 904 (that is, the man) added pleasure as the second user 904 moves the body-extending member 906 inside and outside of (in a reciprocating manner) the fluid-impenetrable receiver 104.

FIG. 9B depicts an end view of an embodiment of an entryway 106 of the fluid-impenetrable receiver 104 FIG. 9A.

In accordance with the embodiment as depicted in FIG. 9B, the entryway 106 provides a flexible slit 114 configured to permit entrance of the body-extending member 906 of the second user 904 (depicted in FIG. 1). The entryway 106 includes a flexible material, and the entryway 106 is defined in the flexible material of the entryway 106.

This written description uses examples to disclose the embodiment of the invention, including the best mode, and also to enable any person skilled in the art to make and use the embodiment of the invention. The patentable scope of the invention is defined by the claims, and may include other examples that occur to those skilled in the art. Such other examples are within the scope of the claims if they have structural elements that do not differ from the literal language of the claims, or if they include equivalent structural elements with insubstantial differences from the literal language of the claims.

It may be appreciated that the assemblies and modules described above may be connected with each other as required to perform desired functions and tasks within the scope of persons of skill in the art to make such combinations and permutations without having to describe each and every one in explicit terms. There is no particular assembly or component that may be superior to any of the equivalents available to the person skilled in the art. There is no particular mode of practicing the disclosed subject matter that is superior to others, so long as the functions may be performed. It is believed that all the crucial aspects of the disclosed subject matter have been provided in this document. It is understood that the scope of the present invention is limited to the scope provided by the independent claim(s), and it is also understood that the scope of the present invention is not limited to: (i) the dependent claims, (ii) the detailed description of the non-limiting embodiments, (iii) the summary, (iv) the abstract, and/or (v) the description provided outside of this document (that is, outside of the instant application as filed, as prosecuted, and/or as granted). It is understood, for this document, that the phrase "includes" is equivalent to the word "comprising." The foregoing has outlined the non-limiting embodiments (examples). The description is made for particular non-limiting embodiments (examples). It is understood that the non-limiting embodiments are merely illustrative as examples.

I claim:

1. An apparatus for sexual activity usage between a first user having a body orifice and a second user having a body-extending member, the apparatus comprising:
　　a garment assembly configured to be worn by the first user, the garment assembly comprising:
　　　　a genital covering portion for covering a genital area of the first user;
　　　　a front panel portion located at one end of the genital covering portion configured to cover a lower abdomen of the first user; and
　　　　a back panel portion located at an end of the genital covering portion opposite to the front panel portion configured to cover buttocks of the first user; and a fluid-impenetrable receiver secured on at least one of the front panel portion and the back panel portion for being located on the first user's lower abdomen and/or buttocks, the fluid-impenetrable receiver forming an entryway configured to receive at least in part the body-extending member of the second user;

wherein the fluid-impenetrable receiver is configured to be spaced apart from and remain entirely outside of the body orifice of the first user as the first user wears the apparatus such that physical contact of the body-extending member of the second user and the body orifice of the first user is prevented and transfer of sexually-transmittable fluid between the first user and the second user is reduced.

2. The apparatus of claim 1, wherein the fluid-impenetrable receiver is configured to be secured to the garment assembly to allow the body-extending member of the second user to be slidably reciprocated into and out from the fluid-impenetrable receiver via the entryway while the fluid-impenetrable receiver remains in a fixed position and orientation relative to the garment assembly.

3. The apparatus of claim 1, wherein the fluid-impenetrable receiver is configured to be spaced apart from the body orifice of the first user so as to be located proximate the body orifice without overlaying the body orifice.

4. The apparatus of claim 1, wherein the fluid-impenetrable receiver defines an interior cavity comprising a sexually-interactive textured material, the interior cavity configured to receive at least in part the body-extending member of the second user.

5. The apparatus of claim 1, wherein the fluid-impenetrable receiver defines an interior cavity comprising a suction element, the interior cavity configured to receive at least in part the body-extending member of the second user.

6. The apparatus of claim 1, wherein the fluid-impenetrable receiver defines an interior cavity comprising a vibrating element, the interior cavity configured to receive at least in part the body-extending member of the second user.

7. The apparatus of claim 1, wherein the fluid-impenetrable receiver defines an interior cavity comprising a heating element, the interior cavity configured to receive at least in part the body-extending member of the second user.

8. The apparatus of claim 1, wherein the garment assembly comprises a fluid-impenetrable material.

9. The apparatus of claim 1, wherein the garment assembly comprises a textured interior portion on the genital covering portion configured to face the genital area of the first user for providing sexual stimulation.

10. The apparatus of claim 1, wherein the garment assembly is configured to be worn at least in part over the genital area of the first user and comprises a heating element on an interior portion, the heating element configured to be located proximate the genital area of the first user.

11. The apparatus of claim 1, wherein the garment assembly is configured to be worn at least in part over the genital area of the first user and comprises a vibrating device on an interior portion, the vibrating device configured to be located proximate the genital area of the first user.

12. The apparatus of claim 1, further comprising a testicle stimulator comprising a sack located proximate to the fluid-impenetrable receiver and configured to contact testicles of the second user when the body-extending member of the second user is received in the fluid-impenetrable receiver.

13. The apparatus of claim 1, wherein the apparatus comprises a body safe material.

14. The apparatus of claim 1, wherein the garment assembly defines underwear.

* * * * *